United States Patent
Scatterday et al.

(10) Patent No.: US 8,875,715 B2
(45) Date of Patent: Nov. 4, 2014

(54) ELECTRONIC CIGARETTE HAVING A FLEXIBLE AND SOFT CONFIGURATION

(71) Applicant: NJOY, Inc., Scottsdale, AZ (US)

(72) Inventors: Mark Scatterday, Scottsdale, AZ (US); Craig Weiss, Scottsdale, AZ (US)

(73) Assignee: NJOY, Inc., Scottsdale, AZ (US)

( * ) Notice: Subject to any disclaimer, the term of this patent is extended or adjusted under 35 U.S.C. 154(b) by 0 days.

(21) Appl. No.: 13/744,092

(22) Filed: Jan. 17, 2013

(65) Prior Publication Data

US 2013/0284191 A1 Oct. 31, 2013

Related U.S. Application Data

(63) Continuation of application No. 13/528,472, filed on Jun. 20, 2012, now abandoned.

(60) Provisional application No. 61/624,056, filed on Apr. 13, 2012, provisional application No. 61/614,973, filed on Mar. 23, 2012.

(51) Int. Cl.
*A24F 47/00* (2006.01)
*A61M 15/06* (2006.01)
*A61M 11/04* (2006.01)

(52) U.S. Cl.
CPC ............. *A24F 47/002* (2013.01); *A61M 15/06* (2013.01); *A24F 47/008* (2013.01); *A61M 11/042* (2014.02); *A61M 2205/8206* (2013.01)
USPC .......... 131/273; 131/365; 128/202.21

(58) Field of Classification Search
USPC ............ 131/270, 273, 194, 328, 329
See application file for complete search history.

(56) References Cited

U.S. PATENT DOCUMENTS

| | | | |
|---|---|---|---|
| 4,771,796 A | 9/1988 | Myer | |
| 7,815,332 B1 * | 10/2010 | Smith | 362/133 |
| 7,886,507 B2 * | 2/2011 | McGuinness, Jr. | 53/504 |
| 2002/0175164 A1 * | 11/2002 | Dees et al. | 220/4.24 |
| 2003/0089377 A1 | 5/2003 | Hajaligol et al. | |
| 2005/0172976 A1 * | 8/2005 | Newman et al. | 131/194 |
| 2006/0150991 A1 | 7/2006 | Lee | |
| 2006/0254948 A1 * | 11/2006 | Herbert et al. | 206/518 |
| 2008/0092912 A1 | 4/2008 | Robinson et al. | |
| 2009/0095311 A1 | 4/2009 | Han | |
| 2009/0267252 A1 * | 10/2009 | Ikeyama | 264/40.1 |

(Continued)

FOREIGN PATENT DOCUMENTS

WO  WO2011/033396 A2 *  3/2011
WO  WO 2011/117580 A2 *  9/2011

*Primary Examiner* — Richard Crispino
*Assistant Examiner* — Eric Yaary
(74) *Attorney, Agent, or Firm* — Bookoff McAndrews, PLLC

(57) ABSTRACT

Generally described, the present disclosure relates to an electronic cigarette intended to more effectively simulate the feel of a traditional cigarette. In one illustrative embodiment, the electronic cigarette can have a flexible and resilient housing, sufficiently strong to protect internal components and sufficient flexible to provide a more realistic user experience to user's accustomed to the pliability of traditional cigarettes. A paper label may be provided, either affixed to the flexible housing or to a prior art, rigid housing. A plastic coating may be providing of the portion of the paper label intended to be inserted into a user's mouth, so as to prevent degradation of the label while at the same time preserving a realistic feel for those portions of the device not intended to be inserted into the mouth.

21 Claims, 1 Drawing Sheet

(56) References Cited

U.S. PATENT DOCUMENTS

| | | |
|---|---|---|
| 2010/0031968 A1* | 2/2010 | Sheikh et al. ............ 131/347 |
| 2010/0186757 A1 | 7/2010 | Crooks et al. |
| 2010/0200006 A1* | 8/2010 | Robinson et al. ......... 131/194 |
| 2010/0242974 A1 | 9/2010 | Pan |
| 2011/0155153 A1* | 6/2011 | Thorens et al. ........... 131/329 |
| 2011/0162667 A1 | 7/2011 | Burke et al. |
| 2011/0168194 A1 | 7/2011 | Hon |
| 2011/0232654 A1 | 9/2011 | Mass |
| 2012/0111347 A1* | 5/2012 | Hon ........................... 131/329 |
| 2012/0204889 A1 | 8/2012 | Xiu |
| 2013/0228191 A1* | 9/2013 | Newton ..................... 131/329 |

* cited by examiner

ELECTRONIC CIGARETTE HAVING A FLEXIBLE AND SOFT CONFIGURATION

CROSS-REFERENCE TO RELATED DISCLOSURES

This disclosure is a continuation of and claims priority to U.S. application Ser. No. 13/528,472, titled ELECTRONIC CIGARETTE HAVING A FLEXIBLE AND SOFT CONFIGURATION that was filed by Craig Weiss and Mark Scatterday on Jun. 20, 2012. This disclosure also claims priority to U.S. Provisional Application Ser. No. 61/624,056 titled SOFT-ENDED ELECTRONIC CIGARETTE to Mark Scatterday that was filed on Apr. 13, 2012 and U.S. Provisional Application Ser. No. 61/614,973 titled ELECTRONIC CIGARETTE ATTACHMENTS, COMPONENTS AND HOLDERS to Craig Weiss and Mark Scatterday that was filed on Mar. 23, 2012.

TECHNICAL FIELD

This disclosure generally relates to electronic cigarettes, and more particularly, to features that make electronic cigarettes more able to mimic a traditional cigarette.

BACKGROUND

Electronic cigarettes currently available on the market are an increasingly popular smoking alternative for smokers of traditional cigarettes. Prior electronic utilize a tubular housing that retains therewithin the device components, which typically include a battery, cartridge, heating element, and a printed circuit. In the prior art, such housings comprise metal or hard plastic, so that the device does not have the precise feel of a traditional cigarette, whether to the user's touch or when placed in the user's mouth.

An electronic cigarette which more closely provides the feel of a traditional cigarette, according to its various embodiments, will be described in the present disclosure.

SUMMARY

This summary is provided to introduce a selection of concepts in a simplified form that are further described below in the DESCRIPTION OF THE APPLICATION. This summary is not intended to identify key features of the claimed subject matter, nor is it intended to be used as an aid in determining the scope of the claimed subject matter.

In accordance with one aspect of the present disclosure, an electronic cigarette is provided. The electronic cigarette comprises: a housing adapted to contain components of an electronic cigarette device; wherein the housing is comprised of a flexible and resilient material capable of protecting the components while allowing the housing to flex when handled by a user.

In accordance with another aspect of the present disclosure, an electronic cigarette is provided. The electronic cigarette comprises: a housing adapted to contain components of an electronic cigarette device; a label adapted to be placed over at least a portion of an exterior of the housing; wherein the label is comprised of paper; a plastic coating positioned over a portion of the label in an area where the label is intended to enter a user's mouth during use.

In accordance with yet another aspect of the present disclosure, an electronic cigarette is provided. The electronic cigarette comprises: a housing adapted to contain components of an electronic cigarette device; wherein the housing is comprised of a flexible and resilient material capable of protecting the components while allowing the housing to flex when handled by a user; a label adapted to be placed over at least a portion of an exterior of the housing; wherein the label is comprised of paper; and a plastic coating positioned over a portion of the label in an area where the label is intended to enter a user's mouth during use.

BRIEF DESCRIPTION OF DRAWINGS

The novel features believed to be characteristic of the application are set forth in the appended claims. In the descriptions that follow, like parts are marked throughout the specification and drawings with the same numerals, respectively. The drawing figures are not necessarily drawn to scale and certain figures can be shown in exaggerated or generalized form in the interest of clarity and conciseness. The disclosure itself, however, as well as a preferred mode of use, further objectives and advantages thereof, will be best understood by reference to the following detailed description of illustrative embodiments when read in conjunction with the accompanying drawings, wherein:

DESCRIPTION OF THE APPLICATION

The description set forth below in connection with the appended drawings is intended as a description of presently preferred embodiments of the disclosure and is not intended to represent the only forms in which the present disclosure can be constructed and/or utilized. The description sets forth the functions and the sequence of steps for constructing and operating the application in connection with the illustrated embodiments. It is to be understood, however, that the same or equivalent functions and sequences can be accomplished by different embodiments that are also intended to be encompassed within the spirit and scope of this application.

Generally described, the present disclosure relates to an electronic cigarette. In one illustrative embodiment, the electronic cigarette can include a flexible yet resilient housing, preferably formed from a suitable plastic material. Through the use of such material, a more tactile feel can be allowed, more accurately simulating the feel of a traditional cigarette, while still suitably protecting the internal device components contained within the housing. In one embodiment, a paper label is provided—whether on a prior art, steel housing, or more preferably, on a flexible housing as described herein—so as to more accurately simulate the paper feel of a traditional cigarette. A number of additional advantages will become apparent from the description provided below.

As will be shown, FIGS. 1 through 4 depict a single-use electronic cigarette. It should be noted, however, that electronic cigarettes consistent with one or more embodiments of the present invention can be provided as a single unit or in multiple pieces, (e.g. with the battery and cartridge comprising separable components), and in the form of a cigar rather than a cigarette.

Figure 1:
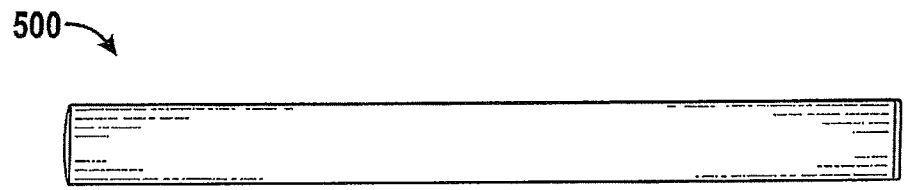
FIG. 1 is a side view of a single-use electronic cigarette in accordance with one or more aspects of the present disclosure.

FIG. 1 is a side view of a single-use electronic cigarette 500 in accordance with one or more aspects of the present disclosure. The device 500, as shown, is provided as a one-piece assembly (i.e., with battery and cartridge both contained within a single housing) and may be disposable after the expiration of the battery or cartridge. When used, the tip of the device 500 can illuminate, simulating the effects of a traditional cigarette, as is known in the art.

Figure 2:
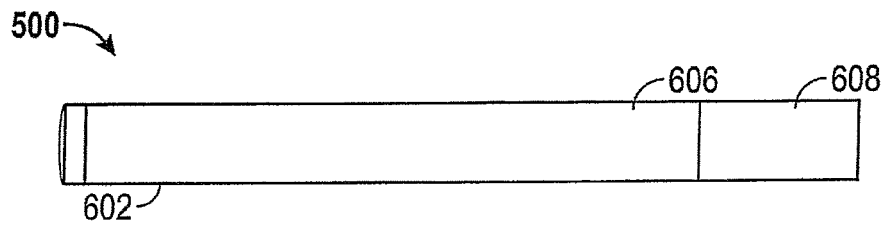
FIG. 2 is a cross-sectional side view of an electronic cigarette in accordance with one or more aspects of the present disclosure.

Referring now to FIG. 2, the electronic cigarette 500 includes a housing 602 that contains the components of the device. This includes the battery 606, heating element and cartridge 608, as well as other components (not shown). The housing 602 must be sufficiently sturdy to provide structural support and also to protect the user from heat generated by the heating element and, as well, to prevent the user from damaging any of the interior components. Typical prior art housings are rigid and are comprised of steel, which provides structural support and which suitably protect the components housed therewithin, covered with a sheet of plastic material. Such a construction, however, is less appealing, from a tactile perspective, to a user of traditional cigarettes, since it is not deformable like a traditional cigarette, lacks the paper covering of a traditional cigarette, and because of its excessive weight as compared to that of a traditional cigarette.

In accordance with an embodiment of the present invention, the prior art rigid housing is replaced with a housing 602 that is flexible, yet resilient—providing sufficient structural integrity and protecting the interior components while also providing users with a device that is flexible, yet resilient, and that is also lighter. One preferred such material is polycarbonate (PC). The use of PC permits the fabrication of a housing that satisfies each of the following criteria: (a) protects interior components; (b) is flexible to the touch, yet resilient; (c) can be provided with an interior diameter large enough to house internal components and an outer diameter small enough to mimic that of a traditional cigarette (approximately 8 mm); and (d) is resistant to heat generated by the heating element.

The use of other synthetic materials, such as polystyrene or polyvinyl chloride, polyethylene, or polypropylene, may also be suitable, though such materials would need to be provided in a greater wall thickness than PC to achieve the objects of the present invention (the desired combination of strength, flexibility, lighter weight, and heat resistance), necessitating a shrinking of the internal device components if a traditional cigarette outer diameter is to be maintained, the provision of an electronic cigarette that is thicker than a traditional cigarette, the provision of an insulation layer, or other modifications.

Figure 3:
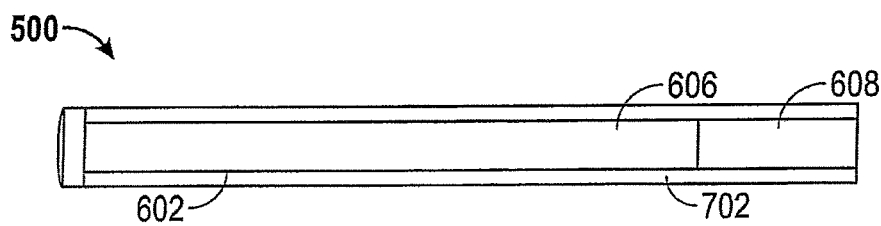
FIG. 3 is a cross-sectional side view of an electronic cigarette in accordance with one or more aspects of the present disclosure.

Referring now to FIG. 3, in one embodiment, a label 702 is provided over all or at least some portion of the housing 602. In some prior art electronic cigarettes, labels are comprised of a sheet plastic type of material, which can be fashioned so as to simulate the appearance of cigarette paper, but which lacks the paper feel of actual cigarette paper. In this embodiment, the label 702 may be provided from a paper material. The label 702 may be provided as a laminate, with an adhesive film layer thereunder, and may be laminated to the exterior surface of the housing 602. Preferably, the label 702 is slightly overlapped, to compensate for manufacturing tolerances.

Additionally, it is preferable to laminate the portion of the label 702 that may enter the mouth of the user during use, generally corresponding to the portion overlaying the cartridge 608, with a plastic such as polypropylene or polyethylene terephthalate. Without such lamination, the label 702 will degrade after coming into contact with the interior of the user's mouth or if it otherwise comes into contact with moisture. At the same time, by providing the lamination only over the portion that contact's the mouth, the remainder of the cigarette 500 retains a paper-like feel and appearance.

In one embodiment, the housing 602 is provided with an interior diameter of approximately 7.7 mm, though an interior diameter in the range of about 7.59 mm to about 7.86 mm would be permissible. The label 702, including the adhesive layer, may have a thickness of approximately 0.09 mm, though a thickness in the range of about 0.06 to about 0.15 mm would be permissible. The polypropylene layer may be provided in a thickness of approximately 0.03 mm, though a thickness in the range of about 0.01 to about 0.06 mm would be permissible. This combination, even allowing for an overlapping of the label 702, permits the construction of an electronic cigarette 500 having the same outer diameter of a traditional cigarette (i.e., approximately 8 mm).

In the preferred embodiment, the label 702 as herein described is placed over a flexible housing 602, as also herein described. It should be noted, however, that substantial benefit may be obtained from providing an electronic cigarette utilizing a prior art, rigid housing, and a paper label 702 as herein described, or by providing a flexible housing 602 as herein described, with a label designed printed thereon or with a plastic label. Any such configuration would provide substantial benefit over prior art devices.

It should be noted that it may be desired to provide an insulation sleeve (not shown) in the interior of housing 602, interposed between the interior diameter of the housing 602 and the internal device components.

Figure 4:
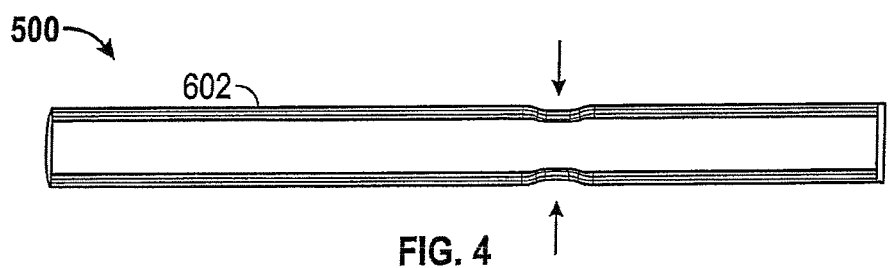
FIG. 4 is a side view of an electronic cigarette in accordance with one or more aspects of the present disclosure.

FIG. 4 is a side view of electronic cigarette 500, illustrating the flexibility provided by the housing 602 as herein described. The device 500, because of the flexible yet resilient qualities of housing 602, can be indented typically anywhere along the length of the device 500. When pressed in, the device 500 can bend at the point of where the pressure was applied. When released, the conduit 500 can return to its normal state.

The foregoing description is provided to enable any person skilled in the relevant art to practice the various embodiments described herein. Various modifications to these embodiments will be readily apparent to those skilled in the relevant art, and generic principles defined herein can be applied to other embodiments. Thus, the claims are not intended to be limited to the embodiments shown and described herein, but are to be accorded the full scope consistent with the language of the claims, wherein reference to an element in the singular is not intended to mean "one and only one" unless specifically stated, but rather "one or more." All structural and functional equivalents to the elements of the various embodiments described throughout this disclosure that are known or later come to be known to those of ordinary skill in the relevant art are expressly incorporated herein by reference and intended to be encompassed by the claims. Moreover, nothing disclosed herein is intended to be dedicated to the public regardless of whether such disclosure is explicitly recited in the claims.

What is claimed is:

1. An electronic cigarette comprising:
    a single housing adapted to contain internal components of the electronic cigarette, the internal components including a battery, a cartridge, and a heating element;
    wherein the single housing is capable of protecting the internal components while allowing the housing to flex when handled by a user; and
    wherein the single housing extends a length of the electronic cigarette from an edge at an end of the electronic cigarette to a tip of the electronic cigarette, wherein the edge is intended to be inserted into a user's mouth during use before any other portion of the electronic cigarette; and a label provided over all of an outer surface of the single housing, and the battery, the cartridge, and the heating element contained within the single housing, wherein the label comprises:
paper; and
a non-paper layer to protect against moisture from the user's mouth;
wherein the non-paper layer is coupled only to a portion of an outer surface of the paper intended to be placed into the user's mouth during use, such that an outermost layer covering a remainder of the single housing is the paper of the label; and
wherein the non-paper layer overlays only a portion of the single housing that contains the cartridge.

2. The electronic cigarette of claim 1 wherein a material of the single housing is polycarbonate, polystyrene, or polyvinylchloride.

3. The electronic cigarette of claim 2 wherein the material is polycarbonate.

4. The electronic cigarette of claim 1 wherein all of the internal components have an outer cross-sectional dimension less than about 7.59 mm.

5. The electronic cigarette of claim 1 wherein the label further comprises an adhesive layer on an underside of the label.

6. An electronic cigarette comprising:
a single housing adapted to contain internal components of the electronic cigarette, the internal components including a battery and a cartridge;
wherein the single housing is capable of protecting the internal components while allowing the single housing to flex when handled by a user;
wherein the material is polycarbonate; and
wherein the single housing extends a length of the electronic cigarette from an edge at an end of the electronic cigarette to a tip of the electronic cigarette, wherein the edge is intended to be inserted into a user's mouth during use before any other portion of the electronic cigarette; and
a label provided over all of an outer surface of the single housing, and the battery and the cartridge contained within the single housing, wherein the label comprises:
paper; and
a non-paper layer to protect against moisture from the user's mouth;
wherein the non-paper layer is coupled only to a portion of an outer surface of the paper intended to be placed into the user's mouth during use, such that an outermost layer covering a remainder of the single housing is the paper of the label; and
wherein the non-paper layer overlays only a portion of the single housing that contains the cartridge;
wherein the electronic cigarette is capable of being indented along the length; and
wherein the electronic cigarette has an outer diameter of approximately 8 mm.

7. The electronic cigarette of claim 6 wherein the single housing has an interior diameter of about 7.59 mm.

8. The electronic cigarette of claim 6 wherein the label further comprises an adhesive layer on an underside of the label; and wherein the non-paper layer is a plastic coating.

9. An electronic cigarette comprising:
a single housing adapted to contain internal components of the electronic cigarette, the internal components including a battery and a cartridge;
wherein the single housing is capable of protecting the internal components while allowing the single housing to flex when handled by a user;
wherein the single housing extends a length of the electronic cigarette from an edge at an end of the electronic cigarette to a tip of the electronic cigarette, wherein the edge is intended to be inserted into a user's mouth during use before any other portion of the electronic cigarette; and
a label provided over all of an outer surface of the single housing, and the battery and the cartridge contained within the housing, wherein the label comprises:
paper;
an adhesive layer on an underside of the label; and
a plastic coating to protect against moisture from the user's mouth;
wherein the plastic coating is coupled only to a portion of an outer surface of the paper intended to be placed into the user's mouth during use, such that an outermost layer covering a remainder of the single housing is the paper of the label; and
wherein the plastic coating overlays only a portion of the single housing that contains the cartridge;
wherein the electronic cigarette bends at a location where a pressure is applied to the single housing; and
wherein the electronic cigarette has an outer diameter of approximately 8 mm.

10. The electronic cigarette of claim 9 wherein a material of the single housing is polycarbonate.

11. The electronic cigarette of claim 9 wherein the label is overlapped.

12. The electronic cigarette of claim 1 wherein the electronic cigarette is capable of being indented along the length.

13. The electronic cigarette of claim 1 wherein the electronic cigarette bends at a location where a pressure is applied to the single housing and is resilient to return to a normal, unbent state after the pressure is released.

14. The electronic cigarette of claim 1 wherein the electronic cigarette is provided as a one-piece assembly.

15. The electronic cigarette of claim 9 wherein the internal components further include a heating element.

16. The electronic cigarette of claim 9 wherein the electronic cigarette is provided as a single unit for use such that the battery and the cartridge are not separable components.

17. An electronic cigarette comprising:
a single housing adapted to contain internal components of the electronic cigarette, the internal components including a battery, a cartridge, and a heating element;
wherein the single housing is flexible, resilient, and comprised of a material capable of protecting the internal components while allowing the single housing to flex when handled by a user;
wherein the material is polycarbonate;
wherein the single housing extends a length of the electronic cigarette from an edge at an end of the electronic cigarette to a tip of the electronic cigarette, the single housing having a substantially constant outer diameter from the edge to the tip, wherein the edge is intended to be inserted into a user's mouth during use before any other portion of the electronic cigarette; and
wherein all of the internal components have an outer cross-sectional dimension less than about 7.59 mm;

a label provided over all of an outer surface of the single housing, and the battery, the cartridge, and the heating element contained within the single housing, wherein the label is overlapped, and wherein the label comprises:
 paper;
 an adhesive layer on an underside of the label; and
 a non-paper layer to protect against moisture from the user's mouth;
 wherein the non-paper layer is coupled only to a portion of an outer surface of the paper intended to be placed into the user's mouth during use, such that an outermost layer covering a remainder of the single housing is the paper of the label; and
 wherein the non-paper layer overlays only a portion of the single housing that contains the cartridge; and
the tip;
 wherein the tip has a curved, convex outer surface facing away from the user's mouth during use; and
 wherein the tip is capable of illuminating during use of the electronic cigarette;
wherein the electronic cigarette has an outer diameter of approximately 8 mm;
wherein the electronic cigarette is capable of being indented along the length; and
wherein the electronic cigarette bends at a location where a pressure is applied to the single housing and is resilient to return to a normal, unbent state after the pressure is released.

18. The electronic cigarette of claim 17 wherein the single housing includes a top edge extending from the edge of the electronic cigarette to the tip of the electronic cigarette, and a bottom edge extending from the edge of the electronic cigarette to the tip of the electronic cigarette, wherein each of the top edge and the bottom edge is continuous from the edge of the electronic cigarette to the tip of the electronic cigarette.

19. The electronic cigarette of claim 1 wherein the single housing has a substantially constant outer diameter from the edge to the tip.

20. The electronic cigarette of claim 6 wherein the single housing has a substantially constant outer diameter from the edge to the tip.

21. The electronic cigarette of claim 9 wherein the single housing has a substantially constant outer diameter from the edge to the tip.

* * * * *